United States Patent [19]

Matsui et al.

[11] Patent Number: 5,017,481
[45] Date of Patent: May 21, 1991

[54] CORYNEFORM BACTERIA CARRYING RECOMBINANT DNA AND PROCESS FOR PRODUCING AN AROMATIC AMINO ACID BY USING THE SAME

[75] Inventors: Kazuhiko Matsui, Kawasaki; Kiyoshi Miwa, Matsudo; Konosuke Sano, Tokyo, all of Japan

[73] Assignee: Ajinomoto Co., Inc., Tokyo, Japan

[21] Appl. No.: 397,370

[22] Filed: Aug. 24, 1989

Related U.S. Application Data

[63] Continuation of Ser. No. 780,256, Sep. 26, 1985, abandoned.

[30] Foreign Application Priority Data

Sep. 27, 1984 [JP] Japan .................. 59-202334

[51] Int. Cl.$^5$ .................. C12N 1/21; C12N 15/52; C12N 15/77; C12P 13/22
[52] U.S. Cl. .................. 435/108; 435/69.1; 435/71.1; 435/91; 435/172.1; 435/172.3; 435/252.32; 435/320.1; 536/27; 935/6; 935/9; 935/22; 935/29; 935/59; 935/60; 935/61; 935/72; 935/73
[58] Field of Search .................. 435/172.1, 172.3, 69.1, 435/91, 108, 252.32, 320; 935/6, 9, 22, 29, 59, 60, 61, 72, 73; 536/27

[56] References Cited

U.S. PATENT DOCUMENTS 4,757,009  7/1988  Sano et al. .................. 435/106

FOREIGN PATENT DOCUMENTS 0077196  4/1983  European Pat. Off. .
2053906  2/1981  United Kingdom .

OTHER PUBLICATIONS

Sugimoto et al., *Agri. Biol. Chem.*, vol. 49, pp. 39–48 (1985).
Nester et al., *J. Bacteriology*, vol. 97, pp. 83–90 (1969).
Sugimoto et al., *J. Biochem.*, vol. 88, pp. 167–176 (1980).
Matsui et al., *Agric. Biol. Chem.*, vol. 52, pp. 525–531 (1988).
Huang et al., #19, pp. 7675–7681, 1975.

*Primary Examiner*—Richard A. Schwartz
*Assistant Examiner*—Richard C. Peet
*Attorney, Agent, or Firm*—Oblon, Spivak, McClelland, Maier & Neustadt

[57] ABSTRACT

A brevibacterium containing a recombinant DNA molecule constructed by operatively connecting a gene coding for shikimate kinase isolated from *Brevibacterium lactofermentum* to a plasmid vector capable of replicating in the *Brevibacterium* is disclosed along with methods of preparing this bacterium and of using it in the production of aromatic amino acids.

14 Claims, 1 Drawing Sheet

CORYNEFORM BACTERIA CARRYING RECOMBINANT DNA AND PROCESS FOR PRODUCING AN AROMATIC AMINO ACID BY USING THE SAME

This application is a continuation of U.S. application Ser. No. 06/780,256, filed on Sept. 26, 1985, now abandoned.

BACKGROUND OF THE INVENTION

1. Field of the Invention

This invention relates to Coryneform bacteria carrying recombinant DNA into which a gene that codes for shikimate kinase has been introduced, and to a process for producing an aromatic amino acid by using the same.

2. Discussion of the Background

Shikimate kinase (hereinafter abbreviated as "SK") is an enzyme that catalyzes conversion of shikimic acid to shikimic acid-3-phosphate. Shikimic acid-3-phosphate thus formed is in turn converted, via chorismic acid, to phenylalanine, tyrosine or tryptophan.

Some examples are mentioned in the scientific literature in which recombinant DNA techniques are used for constructing aromatic-amino-acids-producing bacteria [Japanese Patent Applications Laid-open No. 208,994 (1982), No. 71,397 (1982), No. 89,194 (1983) and No. 134,994 (1983)], but none of these is concerned with a gene that codes for SK (hereinafter referred to as "SK gene").

SUMMARY OF THE INVENTION

It is the object of this invention to obtain microorganisms with higher productivity for aromatic amino acids, and to establish a process for producing aromatic amino acids with higher efficiency, than was previously possible.

This and other objects of the invention as will hereinafter more readily be apparent have been accomplished by providing a Coryneform bacterium carrying a recombinant DNA molecule constructed by connecting a gene coding for shikimate kinase to a plasmid vector capable of replicating in the cells of the Coryneform bacterium. The invention also relates to a process for producing an aromatic amino acid which comprises culturing this Coryneform bacterium in a culture medium and collecting the aromatic amino acid that forms in the medium upon cultivation.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein:

The figure shows the restriction enzyme cleavage map of plasmids pAJ 927 and pAJ 912.

DESCRIPTION OF THE PREFERRED EMBODIMENTS

Figure 1:
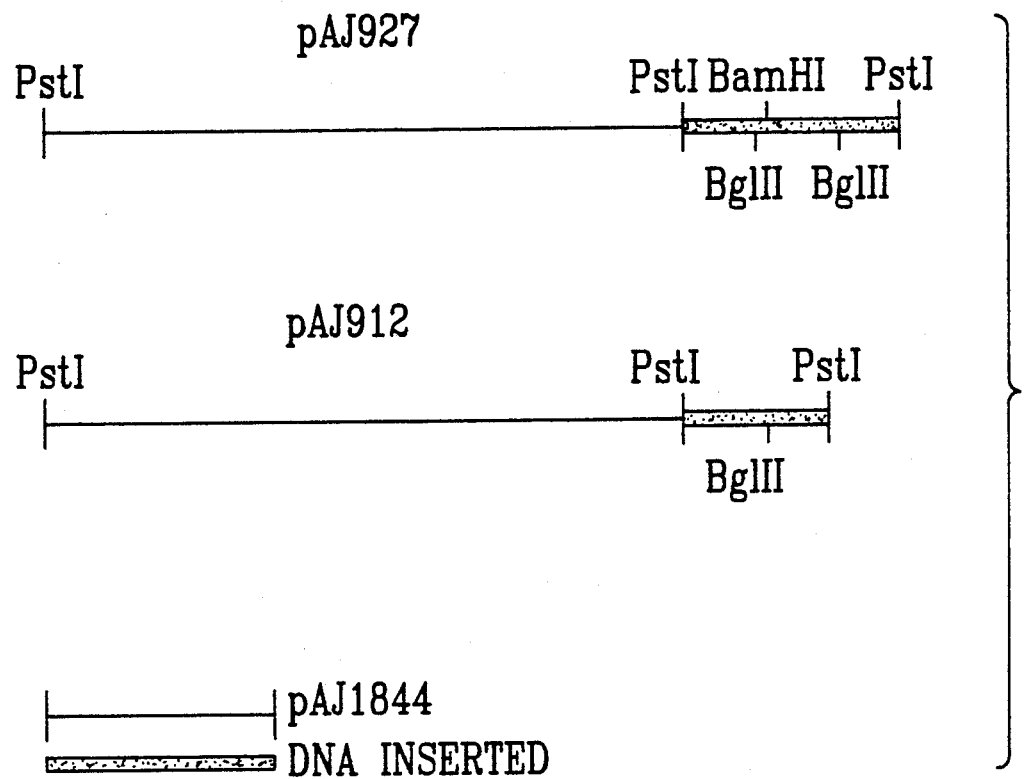

The inventors have succeeded in isolating Coryneform bacteria carrying a recombinant DNA segment in which a gene coding for SK has been inserted into a plasmid vector capable of replicating in the cells of the Coryneform bacterium and have found that the Coryneform bacteria thus obtained have high productivity for one or more aromatic amino acids.

The Coryneform bacteria used in this invention are a group of microorganisms defined beginning on page 599 of Bergey's Manual of Determinative Bacteriology, 8th Edition (1974), which are aerobic, gram-positive, non-acid-fast, non-space forming and rod-shaped bacteria. Of these, the glutamic-acid-producing strains described below are most preferable for the purpose of this invention.

Typical examples of wild strains of Coryneform glutamic-acid-producing bacteria include the following:

| | |
|---|---|
| *Brevibacterium divaricatum* | ATCC 14020 |
| *Brevibacterium saccharoliticum* | ATCC 14066 |
| *Brevibacterium immaliophilum* | ATCC 14068 |
| *Brevibacterium lactofermentum* | ATCC 13869 |
| *Brevibacterium roseum* | ATCC 13825 |
| *Brevibacterium flavum* | ATCC 13826 |
| *Brevibacterium thiogenitalis* | ATCC 19240 |
| *Corynebacterium acetoacidophilum* | ATCC 13870 |
| *Corynebacterium acetoglutamicum* | ATCC 15806 |
| *Corynebacterium callunae* | ATCC 15991 |
| *Corynebacterium glutamicum* | ATCC 13032, 13060 |
| *Corynebacterium lilium* | ATCC 15990 |
| *Corynebacterium melissecola* | ATCC 17965 |
| *Corynebacterium ammoniaphilum* | ATCC 15354 |

Besides these wild strains capable of producing glutamic acid, the Coryneform bacterium used in this invention also include mutant strains therefrom which retain or have lost the ability to produce glutamic acid.

The SK gene may be isolated by the procedure described below or by other known techniques of genetic engineering, now that this gene has been identified.

Chromosomal DNA is extracted from a strain of Coryneform bacterium having an SK gene [e.g., by the method reported in H. Saito and K. Miura; Biochem. Biophys. Acta 72, 619 (1963)] and is then cleaved with a suitable restriction enzyme. The resulting fragment is inserted into a plasmid victor that is capable of replicating in the cells of Coryneform bacteria. The recombinant DNA thus obtained is used to transform an SK-deficient strain of Coryneform bacteria, and strains that have acquired SK activity are selected out. The SK gene can be isolated from these selected strains.

A wide variety of restriction enzymes may be used for cleaving the chromosomal gene if conditions of the cleavage reaction are properly controlled.

Any plasmid vectors that can replicate in the cells of Coryneform bacteria may be used in this invention. Illustrative examples include the following:

(1) pAM 330 Japanese Patent Application Laid-open No. 67,699 (1983)

(2) pAM 1519 Japanese Patent Application Laid-open No. 77,895 (1983)

(3) pAJ 655 Japanese Patent Application Laid-open No. 216,199 (1983) (4) pAJ 611 Japanese Patent Application Laid-open No. 216,199 (1983)

(5) pAJ 1844 Japanese Patent Application Laid-open No. 216,199 (1983)

(6) pCG 1 Japanese Patent Application Laid-open No. 134,500 (1982)

(7) pCG 2 Japanese Patent Application Laid-open No. 35,197 (1983)

(8) pCG 4 Japanese Patent Application Laid-open No. 183,799 (1982)

(9) pCG 11 Japanese Patent Applicatin Laid-open No. 183,799 (1982)

The cleavage of plasmid vector DNA is achieved by using a restriction enzyme which cleaves the DNA only at one site, or by partial digestion with a restriction enzyme capable of cleaving the DNA at several sites.

After the vector DNA and chromosomal DNA are cleaved with the same restriction enzyme, or after otherwise-cleaved fragments of vector and chromosomal DNAs are modified with complementary oligonucleotudes at both ends, the two fragments are subjected to ligation. The two fragments are said to be operatively connected when the resulting recombinant DNA molecule is capable of expressing the SK gene and can reproduce in a host Coryneform bacterium.

The recombinant DNA composed of the chromosomal DNA and vector plasmid DNA fragments thus obtained is then introduced to a Coryneform bacteria by various known techniques. These include: (1) treating the host cells with calcium chloride to enhance their permeability fo DNA, as reported for *Escherichia coli* K-12 [Mandel, M. and Higa, A.; J. Mol. Biiol., 53, 159 (1970)]; (2) introducing DNA to host cells at a specific growth stage that allows easy intake of DNA (the so-called competent cells), as reported for *Bacillus subtilis* [Duncan, C. H., Wilson, G. A. and Young, F. E.; Gene, 1, 153 (1977)]; and (3) use of host cells in the form of protoplast or spheroplast, as known for *Bacillus subtilis*, actinomycetes and yeast [Chang, S. and Cohen, S. N.; Molec. Gen. Genet., 168, 111 (1979); Bibb, M. J. and Hopwood, O. A.: Nature; 274, 398 (1978); Hinnen, A., Hicks, J. B. and Fink, G. R.; Proc. Natl. Acad. Sci. USA, 75, 1929 (1978)].

As for the protoplast method, the above-mentioned technique employed for *Bacillus subtilis* achieves the DNA introduction into Coryneform bacteria with a sufficiently high frequency. However, the technique described in Japanese Patent Application Laid-open No. 183,799 (1982)—introduction of DNA into the protoplast of Brevibacterium or Corynebacterium cells in the presence of polyethylene glycol or polyvinyl alcohol and bivalent metal ions—may also be used for the purpose of this invention. Similar results can be obtained when carboxymethylcellulose, dextran, Ficol or Pluronic (Serva Co.) is used instead of polyethylene glycol or polyvinyl alcohol.

The aromatic-amino-acid producing bacteria of this invention are generally obtained by transformation using SK-deficient strains as a host cell. Strains of high productivity for aromatic amino acids are often derived when the following host cells are selected.

For production of Tyrosine:

A mutant of Corynebacterium requiring phenylalanine for growth and resistant to 3-aminotyrosine, p-aminophenylalanine, p-fluoro phenylalanine and tyrosine hydroxamate [H. Hagino and K. Nakayama; Agric. Biol. Chem., 37, 2013 (1973)]; a mutant of Brevibacterium resistant to m-fluorophenylalanine [Sugimoto, Nakagawa, Tsuchida, Shiido; Agric. Biol. Chem., 37, 2327 (1973)]; and others.

For production of Tryptophan:

A mutant strain of Brevibacterium requiring phenylalanine and tyrosine for growth and resistant to 5-methyltryptophan [I. Shiio, H. Sato, M. Nakazawa; Agric. Biol. Chem., 36, 2315 (1972)]; a mutant strain of Brevibacterium requiring phenylalanine for growth and resistant to m-fluorophenylalanine and 5-fluorotryptophan [I. Shiio, S. Sugimoto, M. Nakagawa, Agric. Biol. Chem., 39, 627 (1975)]; a mutant of Brevibacterium requiring tyrosine for growth and resistant of 5-fluorotryptophan and azaserine; a mutant strain of Corynebacterium requiring phenylalanine and tyrosine for growth and resistant to 5-methyltryptophan, 4-methyltryptophan, 6-fluorotryptophan, tryptophan hydroxamate, p-fluorophenylalanine, tyrosine hydroxamate and phenylalanine hydroxamate [H. Hagino, K. Nakayama; Agric. Biol. Chem., 39, 345 (1975)]; and others.

For production of Phenylalanine:

A mutant strain of Brevibacterium resistant to m-fluorophenylalanine (S. Sugimoto, M. Nakagawa, T. Tsuchida, I. Shiio; Agric. Biol. Chem., 37, 2327 (1973)]; a mutant strain of Brevibacterium requiring tyrosine and methionine for growth and resistant to 5-methyltryptophan and p-fluorophenylalanine [Japanese Patent Application Laid-open No. 116,294 (1974)]; a mutant of Brevibacterium requiring tyrosine and methionine for growth, resistant to 5-methyltryptophan and p-fluorophenylalanine, and sensitive to decoinine [Japanese Patent Application Laid-open No. 64,793 (1981)]; a mutant strain of Corynebacterium requiring tyrosine for growth and resistant to p-fluorophenylalanine and p-aminophenylalanine [H. Hagino, K. Nakayama, Agric. Biol. Chem., 38, 157 (1974)]; and others.

Higher productivity for aromatic amino acids is often observed when other genes are amplified in addition to the SK gene. These include genes that code for 3-dehydroquinate synthase and shikimate dehydrogenase as used in the Example described later, genes that code for 3-deoxy-D-arabino-heptulosonate-7-phosphate (DAHP), a synthetase gene for 5-dehydroquinate dehydratase, a gene for 3-enolpyruvylshikimate-5-phosphate synthetase, and a gene for chorismate synthetase.

When production of tryptophan is intended, better results are often obtained by further amplifying a gene for anthranilate, synthase, a gene for anthranilate phosphoribosyl transferase, a gene for N-(5'-phosphoribosyl)anthranilate isomerase, a gene for indole-3-glycerol phosphate synthase or a gene for tryptophan synthase.

For production of phenylalanine or tyrosine, on the other hand, it is preferable that the transformed strains also contain an amplified gene for prephenate dehydrogenase, prephenate transaminase, pretyrosine dehydrogenase or tyrosine aminotransferase.

The Coryneform bacteria with the ability to produce aromatic amino acids thus obtained may be cultured in much the same way as usual. Ordinary culture media containing carbon sources, nitrogen sources, inorganic ions and, as required, organic micronutrients, such as amino acids and vitamins, are employed. Suitable carbon sources include glucose, sucrose, lactose, starch hydrolyzate containing these sugars, whey and molasses. Preferable nitrogen sources include ammonia gas, ammonia water and ammonium salts. Cultivation is carried out under aerobic conditions at a controlled pH and temperature until the microbial cells cease to produce and accumulate the amino acids in a practical manner.

EXAMPLES (1) Preparation of Chromosomal DNA Containing SK Gene

*Brevibacterium lactofermentum* AJ11225 (FERM-P4370) was inoculated into one liter of CMG medium (containing 1 g/dl peptone, 1 g/dl yeast extract, 0.5 g/dl glucose and 0.5 g/dl NaCl, and having an adjusted pH value of 7.2). Cultivation with shaking was continued at 30° C. for about three hours, and the bacterial cells were collected at their logarithmic growth phase.

The collected cells were lysed with lysozyme/SDS, and the chromosomal DNA was extracted with phenol and purfied in the usual way, giving 3.5 mg of purified DNA.

(2) Preparation of Vector DNA pAJ1844 (M.W.: 5.4 Md) was selected as a suitable vector, and its DNA was isolated as follows:

*Brevibacterium lactofermentum* AJ12037, which contains pAJ1844 as plasmid, was inoculated into 100 ml of CMG medium and grown at 30° C. until the end part of the logarithmic growth phase. The grown cells were lysed with lysozyme/SDS, the resulting mixture was subject to ultracentrifugation (30,000×g, 30 minutes), the supernatant was treated with phenol to extract DNA, and ethanol (twice the volume) was added to precipitate DNA. The DNA thus collected was dissolved in a small amount of TEN buffer (20 mM Tris-HCl, 20 mM NaCl, 1 mM EDTA; pH: 8.0), and then the DNA was separated by electrophoresis in an agarose gel, giving about 15 μg of pAJ1844 plasmid DNA.

(3) Insertion of chromosomal DNA fragment into Vector.

Chromosomal DNA obtained in (1) above (.10 μg) and plasmid DNA obtained in (2) above (5 μg) were separately cleaved with restriction endonuclease Pst I at 37° C. for one hour. After heat treatment at 65° C. for ten minutes, the two reaction mixtures were mixed together, and the ligation reacion was carried out at 10° C. for 24 hours with DNA ligase derived from T phage in the presence of ATP and dithiothreitol. After heat treatment at 65° C. for 5 minutes, ethanol (twice as much by volume) was added, and the precipitate of ligated DNA was collected.

(4) Cloning of SK Gene

*Brevibacterium lactofermentum* AJ12157 deficient in SK gene (a strain requiring phenylalanine, tyrosine and tryptophan for its growth and derived from *Brevibacterium lactofermentum* AJ 12036 by mutation with N-methyl-N-nitro-N-nitrosoguanidine) was used as the DNA recipient.

The protoplast method was employed for transformation. *Brevibacterium lactofermentum* AJ12157 was grown in 5 ml of CMG liquid medium, 0.6 unit/ml of penicillin G was added at the early stage of the logarimthmic growth phase, and cultivation with shaking was further continued for 1.5 hours. The thus-grown bacterial cells were collected by centrifugation, washed with 0.5 ml of SMMP medium (pH 6.5) comprising 0.5M sucrose, 20 mM maleic acid, 20 mM magnesium chloride and 3.5% "Penassay" broth (Difco). Then the cells were suspended in SMMP medium containing 10 mg/ml lysozyme and held at 30° C. for 20 hours. The protoplast thus formed was collected by centrifugation (600×g, 10 minutes) and resuspended in 0.5 ml SMMP medium. The thus-obtained protoplast and 10 μg of DNA prepared in (3) above were mixed with each other in the presence of SmM EDTA, and then polyethylene glycol was added to the mixture to give a final concentration of 30%. The mixture was allowed to stand at room temperature for two minutes. The resulting mixture was washed with 1 ml SMMP medium and then resuspended in 1 ml SMMP medium. The suspension was cultured at 30° C. for two hours. The culture liquid thus obtained was applied on a protoplast regeneration medium (pH 7.0) containing, in one liter of distilled water, 12 g of tris(hydroxymethy)aminomethane, 0.5 g of KCl, 10 g of glucose, 8.1 g of MgCl₂.6H₂O, 2.2 g of CaCl₂.2H₂O, 4 g of peptone, 4 g of powdered yeast extract, 1 g of Casamino acid (Difco), 0.2 g of K₂HPO₄, 135 g of sodium succinate, 8 g of agar, and 3μg/ml chloramphenicol.

After incubation at 30° C. for two weeks, about 25,000 colonies resistant to chloramphenicol appeared, which were transferred by replica plating technique to a minimal medium (2% glucose, 1% ammonium sulfate, 0.3% urea, 0.1% KH₂PO₄, 0.04% MgSO₄.7H₂O, 2 ppm iron ions, 2 ppm manganese ions, 200 μg/1 thiamin hydrochloride, 50μg/1 biotin, 10 μ/1 chloramphenicol, and 1.8% agar; pH 7.0). Thus, five strains which are resistant to chloramphenicol and have lost the property of phenylalanine, tyrosine and tryptophan auxotrophy were obtained.

(5) Analysis of Plasmids in Transformed Strains

Each of the five strains was lysed and the lysate solution was analyzed by electrophoresis on agarose gel in a similar manner to that described in (2) above. As a result of detection of plasmid DNA, a plasmid larger than pAJ 1844 (the vector plasmid) was detected in all of the strains tested.

When the five types of plasmids thus obtained were cleaved with Pst I (the restriction endonuclease used for the DNA recombination), there was observed a DNA fragment 2.9 Kb in size common to all of the five types. This suggests that the SK gene resides in the Pst-I DNA fragment (2.9 Kb). The recombinant plasmid with the 2.9 Kb DNA fragment inserted into the Pst-I cleavage point of vector pAJ1844 was termed AJ927; the recombinant plasmid also having, other than the 2.9 Kb DNA fragment, Pst-I DNA fragments 1.15 and 4.3 Kb in size was termed pAJ1219; the strain carrying pAJ927 was termed AJ12158, FERM-P7865, FERM-BP888; and the strain carrying pAJ1219 was termed AJ12159-FERM-P7866, FERM BP-889.

The mutants identified above by FERM-P numbers were originally deposited on Sept. 22, 1984, and Apr. 5, 1983, at the Fermentation Research Institute, Agency of Industrial Sciences and Technology, Ministry of International Trade and Industry (FRI), 1-3, Migashi 1-Chome, Yatebe-machi, Tsukuba-gun, Ibaragi-ken 305, Japan, and were accorded the FERM-P numbers indicated above. The mutants deposits were then converted into deposits under the Budapest Treaty on Sept. 22, 1985, and were accorded the corresponding FERM-BP numbers.

(6) Re-transformation:

To prove the presence of SK gene on the 2.9 Kb DNA fragment detected in (5) above, *Brevibacterium lactofermentum* AJ12157 was again transformed by using pAJ1219 and pAJ927.

Of the chloroamphenicol resistant colonies, ten colonies were picked up and tested for phenylalanine, tyrosine and tryptophan auxotrophy. It was found that each colony tested has lost this auxotrophic property, clearly indicating the presence of SK gene on the above-mentioned recombinant plasmids.

(7) SK Activity of Transformed Strains

The transformed strain being tested was cultured in 20 ml of a standard medium for tryptophan production (130 g/1 glucose, 25 g/1 (NH₄)₂SO₄, 1 g/1 KH₂PO₄, 1 g/1 MgSO₄.7H₂O, 12 g/1 fumaric acid, 3 ml/1 acetic acid, 50 ml/1 "Mi-eki" (hydrolyzate of soy protein), 10 mg/1 MnSO₄.4H₂O, 50 μg/1 biotin, 2000 μg/1 Thiamin hydrochloride and 50 g/1 CaCO₃: pH 6.5) at 30° C. for 22 hours. The thus-grown cells were lysed by ultrasonic treatment, the resulting mixture was centrifuged (32000×g, 20 minutes), and the supernatant (crude enzyme solution) was allowed to react, at 30° C. for 30 minutes, with a solution containing 50mM veronal buffer (pH 9.0), 1 mM shikimic acid, 4 mM ATP, 5 mM $MgCl_2$ and 10 mM NaF. When reaction was complete, 0.2 ml of 1M Tris-HCl buffer (pH 7.8) was added, and the mixture was heated at 100° C. for two minutes to inactivate the enzyme. After cooling, 3.0 ml of solution (appropriately diluted to a shikimic acid content of 2 to 10 μg ) was taken, 0.5 mol of 1% periodic acid solution was added, and the mixture allowed to stand at room temperature for three hours. The amount of shikimic acid was determined by adding 0.5 ml of 1N NaOH (aq.) and 0.3 ml of 0.1M glycine solution and measuring absorbance at 380 nm. SK activity was calculated from the difference in the amount of shikimic acid before and after reaction. The result is summarized in Table 1.

TABLE 1

| Strain | SK Activity (nmol/mg-protein/min) |
|---|---|
| *Brevibacterium lactofermentum* AJ12036 | 3.5 |
| *Brevibacterium lactofermentum* AJ12158 FERM BP-888 | 33.5 |
| *Brevibacterium lactofermentum* AJ12159 FERM BP-889 | 42.9 |

(8) Recombinant Plasmids
(Identification of Shikimate Dehydrogenase Gene and 3-Dehydroquinate Synthase Gene on pAJ927 and pAJ1219)

Plasmids pAJ927 and pAJ1219 were introduced into shikimate-dehydrogenase-deficient strain AB2834 and 3-dehydroquinate-synthase-deficient strain AB2847 (both derived from *Escherichia coli* K12; J. Pittard et al.; J. Bacteriol., 91, 1494, 1966).

Transformation was effected by treatment of recipient cells with calcium chloride. Of the chloramphenicol-resistant colonies, ten colonies were picked up and tested for the property of phenylalanine, tyrosine and tryptophan auxotrophy. It was found that both pAJ927 and pAJ1219 caused AB2847 to lose the auxotropic property. With AB2834, on the other hand, no such change was observed after transformation with pAJ927, but the auxotropic property was lost after transformation with pAJ1219.

This indicates that pAJ927 carries cloned SK gene and 3-dehydroquinate synthase gene on the inserted Pst-I DNA fragment 2.9 Kb) and that pAJ1219 has cloned SK gene, 3-dehydroquinate synthase gene, and shikimate dehydrogenase gene.

(9) Shikimate Dehydrogenase Activity of Transformed Strains

Crude enzyme solutions were prepared from AJ12036 (wild strain) and AJ12159 (transformed strain) by the method used in (7) above.

Each of these crude enzyme solutions was added to a mixture of 0.1M Tris-HCl buffer (pH 7.4), 0.8 mM NADP and 4 mM shikimic acid, and shikimate dehydrogenase activity was determined by measuring the change in optical density at 300 mμ resulting from the conversion of NADH.

TABLE 2

| Strain | Shikimate Dehydrogenase Activity |
|---|---|
| *Brevibacterium lactofermentum* AJ12036 | 22.1 nmol/mg-protein/min |
| *Brevibacterium lactofermentum* | 44.1 |

TABLE 2-continued

| Strain | Shikimate Dehydrogenase Activity |
|---|---|
| AJ12159 FERM BP-889 | |

(10) Sub-cloning of SK Gene

Plasmid pAJ927 was completely cleaved with restriction enzyme Bgl II. After the solution was heated at 65° C. for ten minutes, ATP, dithiothreitol, and DNA ligase derived from T4 phage were added, and the ligation reaction was carried out at 10° C. for 16 hours. After this solution was heated at 65° C. for ten minutes, ethanol (twice as much by volume) was added, and the precipitate of ligated DNA was collected. This was suspended in TEN buffer and cleaved with restriction enzyme BamH I. After this solution was heated at 65° C. for ten minutes, ethanol (twice as much by volume) was added, and the precipitate of DNA which separated out was collected and dissolved in TEN buffer to be used for transformation.

*Brevibacterium lactofermentum* AJ12157 was transformed by the method used in (4) above. After incubation at 30° C. for two weeks on the regeneration medium containing 3 μg/ml chloramphenicol, the thus-grown cells were transferred to a minimal medium by the replica plating technique, affording many strains which are resistance to chloramphenicol and have lost the natural phenylalanine, tyrosine and tryptophan auxotrophy. All of these strains contained pAJ912, a plasmid smaller than pAJ927. Plasmids pAJ927 and pAJ912 have the restriction enzyme cleavage maps as shown in the Figure.

AJ12157 was again transformed by pAJ912, and chloramphenicol resistant colonies were picked up. It was demonstrated that all of these had lost the property of phenylalanine, tyrosine and tryptophan auxotrophy. This indicates the presence of the SK gene on pAJ912.

Plasmid pAJ912 was then used to transform AB2847, a mutant of *Escherichia coli* K12 deficient in 3-dehydroquinate synthase. Chloramphenicol resistant colonies thus formed where picked up and tested for the property of phenylalanine auxotrophy. This property was restored in none of these transformed strains, suggesting that pAJ912 has partly or completely lost the 3-dehydroquinate synthase gene.

(11) Tryptophan Productivity of Transformed Strains

*Corynebacterium glutamicum* (ATCC 13060) and *Brevibacterium lactofermentum* M247, resistant to m-fluorophenylalanine and 5-fluorotyrosine, were transformed by pAJ927, pAJ912 and pAJ1219 according to the method used in (4) above. Chloramphenicol-resistant, transformed strains thus screened out were AJ12160 (FERM-p7867 FERM BP-890), AJ12161 (FERM-P 7868 FERM BP-891) AJ12169 (FERM-P7869 FERM BP-892), AJ12170 (FERM-P7870 FERM BP-893) and AJ12171 (FERM-P7871 FERM BP-894). The mutants identified above by FERM-P numbers were originally deposited on Sept. 22, 1984 at the Fermentation Research Institute, Agency of Industrial Sciences and Technology, Ministry of International Trade and Industry (FRI), 1-3, Migashi 1 Chome, Yatebe-machi, tsukuba-gun, Ibaragi-ken 305, Japan, and were accorded the FERM-P number indicated above. The mutants deposits were then converted into deposites under the Budapest Treaty on Sept. 22, 1985, and were accorded the corresponding FERM-BP numbers, Tryptophan productivity of these strains is summarized in Table 3.

Each strain was inoculated to 20 ml of a standard medium for tryptophan production (130 g/l of glucose, 25 g/l (NH$_4$)$_2$SO$_4$ 12 g/l fumaric acid, 3 ml/l acetic acid, 1 g/l KH$_2$PO$_4$, 10 mg/l MnSO$_4$.7H$_2$O, 50 g/l d-biotin, 200 μg/l thiamin hydrochloride, 400 ml/l methionine, 650 mg/l tyrosine, 50 ml/l "Mi-eki" (hydrolyzate of soy protein) and 50 g/l CaCO$_3$; pH (6.5). Cultivation with shaking was continued at 30° C. for 72 hours, and the content of L-tryptophan in the supernatant was determined by a bio-assay using *Leuconostoc mesenteroides* ATCC 8042.

TABLE 3

L-tryptophan Productivity of Transformed Strains

| Strain | Amt. of L-tryptophan Accumulated |
|---|---|
| *Brevibacterium lactofermentum* M247 | 0.16 g/dl |
| *Brevibacterium lactofermentum* AJ12171 (M247/pAJ912) FERM BP-894 | 0.33 g/dl |
| *Brevibacterium lactofermentum* AJ12160 (M247/pAJ927) FERM BP-890 | 0.40 g/dl |
| *Brevibacterium lactofermentum* AJ12161 (M247/pAJ1219) FERM BP-891 | 0.46 g/dl |
| *Corynebacterium glutamicum* AJ12169 (ATCC13060/pAJ927) FERM BP-892 | 6 mg/dl |
| *Corynebacterium glutamicum* AJ12170 (ATCC13060/pAJ1219) FERM BP-893 | 8 mg/dl |

In order to obtain AJ12157 and M247, it is possible to cure composite plasmids from AJ12158 and AJ12160 without damaging the host cells. Plasmids may be lost spontaneously from host cells or can be artificially eliminated by a curing operation [Bact. Rev., 56, p361–405 (1972). For example, AJ12158 (AJ12160) is inoculated to CMG liquid medium and cultivated at 37° C. (high temperature treatment) for one night. The culture liquid was appropriately diluted, applied on CMG agar medium containing or not containing chloramphenicol, and incubated at 30° C. for one to three days. AJ12157 (M247) can thus be screened out as a chloramphenicol sensitive strain.

All publications cited in this specification are indicative of the level of skill of those skilled in the art to which this invention pertains. Each publication is individually incorporated herein by reference in the location where it is cited.

Obviously, numerous additional modifications and variations of the present invention are possible in light of the above teachings. It is therefore to be understood that within the scope of the appended claims, the invention may be practiced otherwise than as specifically described herein.

What is claimed and desired to be secured by Letters Patent of the United States:

1. A transformed bacterium selected from the genus Brevibacterium containing a recombinant DNA molecule constructed by connecting a gene coding for shikimate kinase isolated from a source bacterium selected from the species *Brevibacterium lactofermentum* to a plasmid vector capable of replicating in said transformed bacterium so that said gene can be expressed in said transformed bacterium.

2. The transformed bacterium of claim 1, wherein said recombinant DNA molecule further comprises a gene coding for 3-dehydroquinate synthase or shikimate dehydrogenase isolated from a bacterium selected from the species *Brevibacterium lactofermentum*.

3. The transformed bacterium of claim 1, wherein before transformation, said bacterium requires phenylalanine, tyrosine, or methionine for growth.

4. The transformed bacterium of claim 1, wherein said transformed bacterium is resistant to 3-aminotyrosine, p-aminophenylalanine, p-fluorophenylalanine, tyrosine hydroxamate, or m-fluorophenylalanine.

5. The transformed bacterium of claim 1, wherein said transformed bacterium is resistant to 5-methyltryptophan, 5-fluorotryptophan, azaserine, 5-methyltryptophan, 4-methyltryptophan, 6-fluorotryptophan, tryptophan hydroxamate or phenylalanine hydroxamate.

6. The transformed bacterium of claim 1, wherein said transformed bacterium is sensitive to decoinine.

7. A recombinant DNA molecule, wherein said molecule comprises a gene coding for shikimate kinase isolated from a bacterium selected from the species *Brevibacterium lactofermentum* connected to a DNA segment capable of acting as a plasmid vector, wherein said recombinant DNA molecule is capable of replicating said recombinant DNA molecule in a bacterium selected from the genus Brevibacterium and is capable of producing shikimate kinase.

8. The recombinant DNA molecule of claim 7, wherein said molecule further comprises a gene coding for 3-dehydroquinate synthase of shikimate dehydrogenase isolated from a bacterium selected from the species *Brevibacterium lactofermentum*.

9. A process for producing an aromatic amino acid, which comprises:
 culturing a bacterium selected from the genus Brevibacterium containing a recombinant DNA molecule constructed by operatively connecting a gene coding for shikimate kinase isolated from *Brevibacterium lactofermentum* to a plasmid vector capable of replicating in said bacterium, and
 collecting the aromatic amino acid which accumulates in the culture medium.

10. The process of claim 9, wherein said aromatic amino acid is tyrosine.

11. The process of claim 9, wherein said aromatic amino acid is phenylalanine.

12. The process of claim 9, wherein said aromatic amino acid is tryptophan.

13. A plasmid selected from the group consisting of pAJ912, pAJ927, and pAJ1219.

14. A microorganism selected from the group consisting of *Brevibacterium lactofermentum* AJ12158 FERM BP-888, *Brevibacterium lactofermentum* AJ12159 FERM BP-889, *Brevibacterium lactofermentum* AJ12171 FERM BP-894, *Brevibacterium lactofermentum* AJ12160 FERM BP-890, *Brevibacterium lactofermentum* AJ12161 FERM BP-891, *Corynebacterium glutamicum* AJ12169 FERM BP-892, and *Corynebacterium glutamicum* AJ12170 FERM BP-893.

* * * * *